United States Patent
Gelman et al.

(10) Patent No.: US 11,248,018 B2
(45) Date of Patent: Feb. 15, 2022

(54) PROCESS FOR PREPARATION OF NICOTINAMIDE RIBOSIDE (NR) AND COSMETIC COMPOSITION COMPRISING (NR AND A PHOSPHATE-BINDING AGENT

(71) Applicants: YISSUM RESEARCH DEVELOPMENT COMPANY OF THE HEBREW UNIVERSITY OF JERUSALEM LTD., Jerusalem (IL); HIKARI LABORATORIES LTD., Bnei Atarot (IL)

(72) Inventors: Dmitri Gelman, Mevasseret Zion (IL); Amani Zoabi, Nazareth (IL); Assaf Zeira, Nir Zvi (IL); Raed Abu-Reziq, Jatt Hamesholash (IL)

(73) Assignees: YISSUM RESEARCH DEVELOPMENT COMPANY OF THE HEBREW UNIVERSITY OF JERUSALEM LTD., Jerusalem (IL); HIKARI LABORATORIES LTD., Bnei Atarot (IL)

( * ) Notice: Subject to any disclaimer, the term of this patent is extended or adjusted under 35 U.S.C. 154(b) by 0 days.

(21) Appl. No.: 16/078,320

(22) PCT Filed: Feb. 21, 2017

(86) PCT No.: PCT/IL2017/050219
§ 371 (c)(1),
(2) Date: Aug. 21, 2018

(87) PCT Pub. No.: WO2017/145151
PCT Pub. Date: Aug. 31, 2017

(65) Prior Publication Data
US 2019/0055275 A1 Feb. 21, 2019

Related U.S. Application Data

(60) Provisional application No. 62/298,480, filed on Feb. 23, 2016.

(51) Int. Cl.
*C07H 19/048* (2006.01)
*C07H 1/00* (2006.01)
*A61K 8/60* (2006.01)
*A61Q 19/08* (2006.01)
*A61K 8/02* (2006.01)

(52) U.S. Cl.
CPC ......... *C07H 19/048* (2013.01); *A61K 8/0241* (2013.01); *A61K 8/606* (2013.01); *A61Q 19/08* (2013.01); *C07H 1/00* (2013.01); *A61K 2800/412* (2013.01)

(58) Field of Classification Search
CPC ................................ C07H 19/048; C07H 1/00
See application file for complete search history.

(56) References Cited

U.S. PATENT DOCUMENTS

2017/0121746 A1* 5/2017 Velasquez ............... C12P 19/28

FOREIGN PATENT DOCUMENTS

| WO | WO 2006/105440 | 10/2006 |
| WO | WO 2010/015827 | 2/2010 |
| WO | WO 2015/014722 | 2/2015 |

OTHER PUBLICATIONS

Ora, M. et al. JOC, "Bisphosphonate Derivatives of Nucleoside Antimetabolites: Hydrolytic Stability and Hydroxyapatite Adsorption of 5'-beta-gamma-Methylene and 5'-beta,gamma-(1-hydroxyethylidene) Triphosphates of 5-fluorouridine and ara-Cytidine", 2008, vol. 73, pp. 4123-4130 (Year: 2008).*
International Search Report issued in PCT/IL2017/050219 dated Aug. 5, 2017.
Written Opinion of the International Searching Authority issued in PCT/IL2017/050219 dated Aug. 5, 2017.
Franchetti et al., "Stereoselective synthesis of nicotinamide β-riboside and nucleoside analogs" *Bioorganic & Medicinal Chemistry Letters*, 14(18): 4655-1658 (2004).
Friedlos et al., "Identification of Novel Reduced Pyridinium derivatives as synthetic co-factors for the enzyme DT diaphorase (NAD(P)H Dehydrogenase (Quinone), EC 1.6.99.2)" *Biochemical Pharmacology*, 44 (1): 25-31 (1992).
Karrer et al., "Kristallisiertes 3-Carbonsureamid-$N^1$-$_D$-Ribosido-Pyridiniumbromid und Verwandte Verbindungen" *Biochimica et Biophysica Acta*, vol. 12 (1953), pp. 51-55.
Lee et al., "A chemical synthesis of nicotinamide adenine dinucleotide ($NAD^+$)" *Chem. Commun.*, 1999, 729-730.
Liu et al., "A Novel Preparation of Nicotinamide Mononucleotide" *Nucleosides & Nucleotides*, 13(5), 1215-1216 (1994).
Tanimori et al., "An Efficient Chemical Synthesis of Nicotinamide Riboside (NAR) and Analogues" *Bioorganic & Medicinal Chemistry Letters*, 12(8): 1135-1137 (2002).

* cited by examiner

*Primary Examiner* — Bahar Craigo
(74) *Attorney, Agent, or Firm* — Nixon & Vanderhye PC

(57) ABSTRACT

Disclosed herein is a process for preparing nicotinamide riboside (NR) from an NR precursor and a phosphate-binding agent in a solvent. The reaction-derived mixture comprising NR may be further used without further processing in a variety of products, particularly in a cosmetic product.

6 Claims, No Drawings

PROCESS FOR PREPARATION OF NICOTINAMIDE RIBOSIDE (NR) AND COSMETIC COMPOSITION COMPRISING (NR AND A PHOSPHATE-BINDING AGENT

This application is the U.S. national phase of International Application No. PCT/IL2017/050219 filed 21 Feb. 2017, which designated the U.S. and claims the benefit of U.S. Provisional Application No. 62/298,480 filed 23 Feb. 2016, the entire contents of each of which are hereby incorporated by reference.

The invention relates to nicotinamide riboside (NR), its preparation and use thereof, especially in cosmetic, nutraceutical and pharmaceutical applications.

1-(β-D-Ribofuranosyl)-nicotinamide [nicotinamide riboside (NR)] is a nucleoside, which incorporates nicotinamide and ribose into a single structural motif where the positively charged pyridinium moiety is balanced with a negatively charged counter ion (Formula A). The nature of the counter ion depends on the synthesis or production procedure. The most common counter ions include, but are not limited to, halide (Cl$^-$, Br$^-$), acetate, phosphate and trifluoromethanesulfonate. In Formula A depicted below, the counter ion is designated X$^-$ for the purpose of illustration; it does necessarily have to be a monovalent anion.

(Formula A)

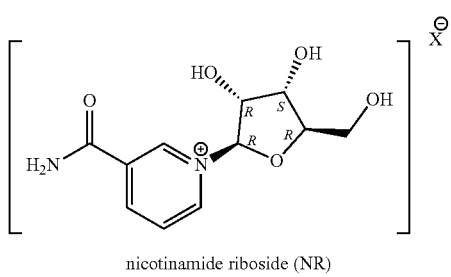

nicotinamide riboside (NR)

Nicotinamide riboside naturally occurs in yeast, bacteria, and mammals. Therefore, often, nicotinamide riboside is produced biotechnologically from yeast.

Chemical syntheses normally rely on ribosilation of niacin or its derivatives with fully protected ribose (see Scheme 1).

(Scheme 1)

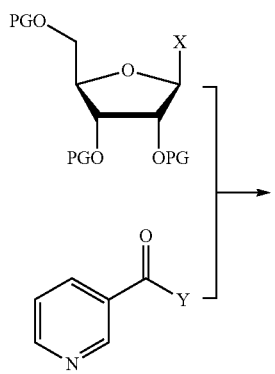

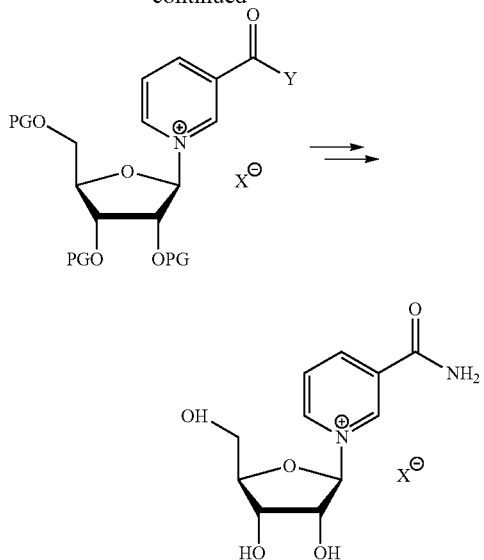

PG - protecting group
X - Br, Cl, OTf, OAc
Y - NH$_2$, OR

For example, the first synthesis of NR was suggested in early 50's where the tetraacetylribose (PG=OAc) was treated with niacinamide in HBr. The HBr treatment results in the formation of NR (X=Br) in low to moderate yield (10-30%). The synthesis is not reliable: the product was not properly analyzed in terms of the stereopurity—most probably β-to-α epimerization of the ribose residue takes place, and the product was apparently obtained as a mixture of the stereoisomers (Karrer, P. et al. Crystalline N-ribosidonicotinamide bromide and related compounds. Biochim. Biophys. Acta 1953, 12, 51-5).

More recent syntheses of NR took advantage of the costly, yet efficient, trimethylsilyl-trifluoromethane sulfonate reagent (TMSOTf; CAS Registry Number 27607-77-8) instead of HBr. The synthesis is reliable, resulting in the formation of NR balanced with trifluoromethanesulfonate counter ion (X=OTf) in ca. 60% yield after base-promoted hydrolysis of the triacetylated intermediate (Tanimori, S. et al. Bioorganic & Medicinal Chemistry Letters 2002, 12, 1135-1137; Lee, J. et al. Chem. Commun. (Cambridge) 1999, 729-730; Franchetti, P. et al., Bioorg. Med. Chem. Lett. 2004, 14, 4655-4658; WO 2006/105440; and WO 2015/014722).

There is still a need for a chemical synthesis process for the preparation of nicotinamide riboside that will improve the yield and/or will reduce the production costs.

Zirconium tetrachloride (ZrCl$_4$)-promoted hydrolysis of β-nicotinamide adenine dinucleotide [abbreviated "NAD$^+$"] to the β-nicotinamide mononucleotide [abbreviated "NMN"], and adenine monophosphate (the primary NAD$^-$ hydrolysis) is known (Liu R. and Visscher J. "*A novel preparation of nicotinamide mononucleotide*", Nucleosides and Nucleotides, 13(5), 1215-1216, (1994)), as shown in Scheme 2 below:

(Scheme 2)

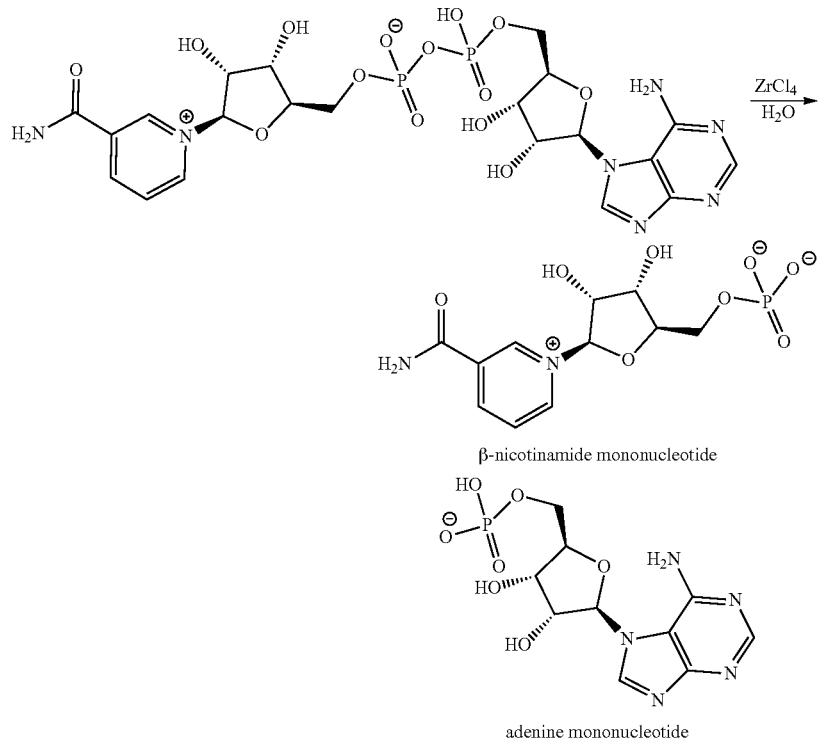

β-nicotinamide mononucleotide adenine mononucleotide

It has now been found that NR can be produced via controllable degradation of $NAD^+$ in solution, advanced through the removal of the phosphate ion from the solution, e.g., the degradation reaction of $NAD^+$ takes place in an aqueous solution in the presence of a phosphate-binding agent, which drives the hydrolysis of β-nicotinamide mononucleotide to the target β-nicotinamide riboside (named herein the "secondary hydrolysis"). The presence of zirconium tetrachloride or similar reagents affecting the primary $NAD^+$ hydrolysis is not essential. In fact, in the absence of zirconium tetrachloride, the resultant aqueous mixture, e.g. solution, may be directly processed into a useful product, without isolating the NR product from the solution, thereby minimizing downstream processing. Similarly, β-nicotinamide mononucleotide may be used as a starting material and converted into β-nicotinamide riboside-containing solution. The product may be, for example, an oral dosage form, such as a capsule or a tablet, a topical dermal dosage form, for example, a cosmetic preparation, or a or transdermal dosage form. Alternatively, the aqueous solution may be processed to furnish an encapsulated mixture of the ingredients of the aqueous solution, e.g. into micro-gel beads or sol-gel microcapsules, to be further processed into useful dosage forms.

Accordingly, the invention is primarily directed to a process for preparing nicotinamide riboside (NR), comprising combining nicotinamide riboside precursor, e.g. β-nicotinamide adenine dinucleotide ($NAD^+$) and/or β-nicotinamide mononucleotide, with a phosphate-binding agent in a solvent.

The term "phosphate-binding agent" refers to a chemical species that is capable of removing the phosphate anion from the solution, for example, the phosphate-binding agent is a metal cation $M^{(n+)}$ which combines with phosphate to form water insoluble, or sparingly water soluble, phosphate salt. Examples of such metal cations which are suitable for use in the invention, and the respective solubility-product constants ($K_{sp}$) of their phosphate salts, include—but are not limited to—alkaline earth metals such as $Ca^{(2+)}[K_{sp}=2.07\times 10^{-33}]$, $Mg^{(2+)}[K_{sp}=1.04\times 10^{-24}]$ and $Ba^{(2+)}[K_{sp}=3.40\times 10^{-23}]$; $Al^{(3-)}[K_{sp}=9.84\times 10^{-21}]$; and transition-metal elements, e.g. $Co^{(2+)}[K_{sp}=2.05\times 10^{-35}]$, $Cu^{(2-)}[K_{sp}=1.40\times 10^{37}]$, $Cd^{(2+)}[K_{sp}=2.53\times 10^{\times 33}]$ and $Fe^{(3+)}[K_{sp}=9.91\times 10^{-16}]$. Preferably the phosphate binding agent is $Ca^{(2-)}$.

The phosphate-binding agent, that is, the metal cation set forth above, is added to the solution in the form of a water soluble salt thereof (hereinafter "a source of a phosphate-binding agent") which dissociates and releases the metal ion in the solution. By the term "water soluble salt" is preferably meant a salt with solubility exceeding 3 g per 100 g water, or exceeding 5 g per 100 g of water, or exceeding 10 g per 100 g of water, or exceeding 15 g per 100 g water, or exceeding 20 g per 100 g of water, or exceeding 25 g per 100 g of water, or exceeding 30 g per 100 g water at room temperature (18-25° C.). Especially preferred are water-soluble $Ca^{(2+)}$ salts, such as calcium L-ascorbate, calcium acetate, calcium citrate, calcium gluconate, calcium lactate, and calcium halide, e.g. calcium chloride.

Similarly, β-nicotinamide mononucleotide may also be produced by hydrolysis of $NAD^+$ under primary hydrolysis route, e.g. by heating of $NAD^+$ aqueous solution in presence of zirconium reagents, e.g. zirconium dioxide ($ZrO_2$), zirconium tetrachloride ($ZrCl_4$), zirconium diphosphate ($Zr(HPO_4)_2$), zirconium carbonate ($Zr(CO_3)_2$), zirconium hydroxide ($Zr(OH)_4$) or zirconium sulfate ($Zr(SO_4)_2$). Preferably, zirconium reagent is zirconium dioxide. When zirconium dioxide is used, it may be removed from the reaction mixture by centrifugation. The solution may be further used, e.g. in secondary hydrolysis to furnish nicotinamide riboside solution.

Thus, nicotinamide riboside precursor, e.g. β-nicotinamide adenine dinucleotide (NAD⁻) and/or β-nicotinamide concentration due to extensive decomposition of NR to ribose and nicotinamide (Vitamin PP):

(Scheme 3)

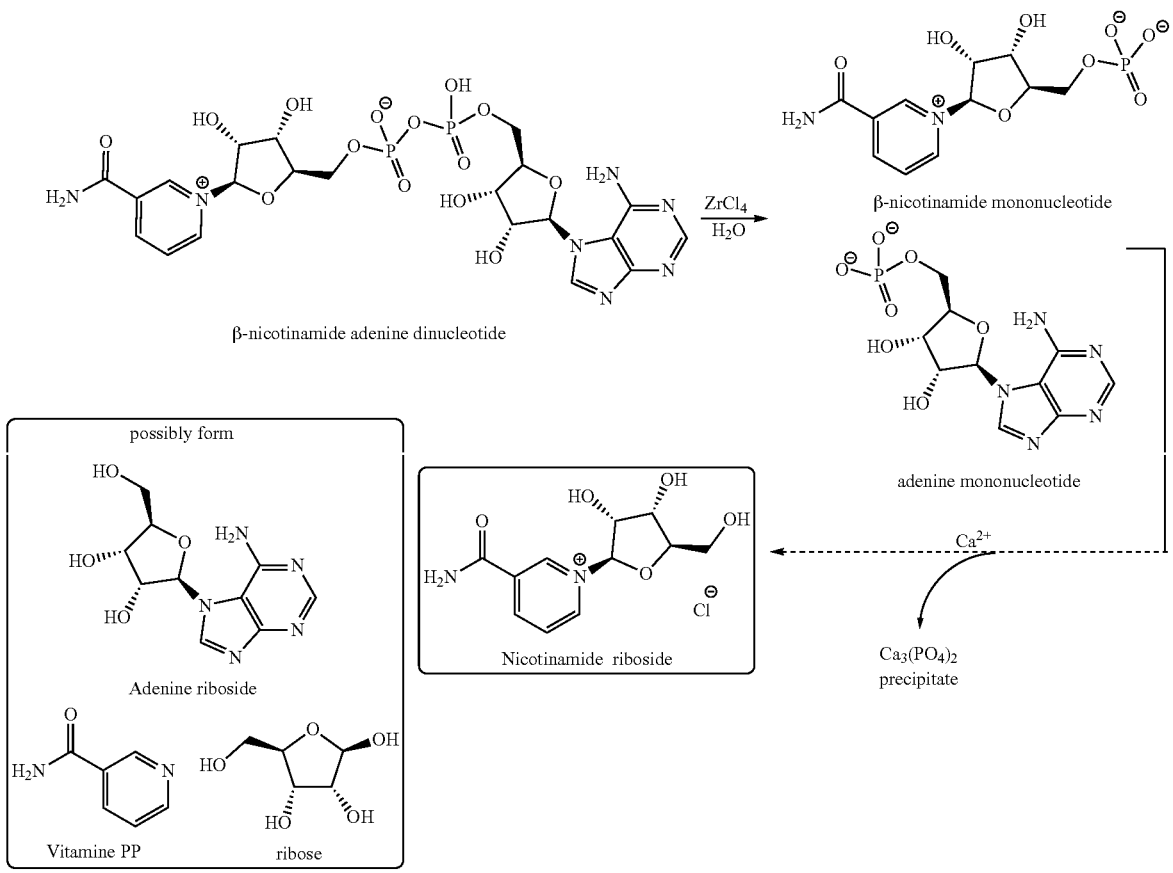

mononucleotide, and a source of phosphate-binding agent are combined together in a solvent in a reaction vessel at a suitable molar ratio, for example, of about 1:2 to 1:15, e.g. between 1:3 and 1:12, or between 1:6 to 1:10, inclusive.

The so-formed solution may be heated, preferably at a temperature in the range from 40 to 90° C., preferably at 50-80° C., inclusive. The heating may be performed for not less than 12 hours, e.g. for 24 hours, or for 48 hours, preferably for 48 hours, optionally under stirring, in particular when the nicotinamide riboside precursor is NAD⁺.

The reaction takes place in a solvent. Suitable solvents include water or aqueous alcohol. Water is especially preferred. Alcohols suitable as a solvent in an aqueous solution include ethanol, methanol and isopropanol. The typical concentration of alcohols in the solvent is below 1%-30% % w/v, preferably below 10%.

As mentioned above, when NAD⁺ is used as nicotinamide riboside precursor, the presence of zirconium tetrachloride or other agents useful in promoting the primary hydrolysis of NAD⁺ is not mandatory. However, if such an agent is used, then it is preferably added to the reaction mixture simultaneously with the source of the phosphate-binding agent. Experimental work performed in support of this invention indicates that a successive mode of addition (first zirconium tetrachloride to advance the primary hydrolysis, with the phosphate-binding agent being added only after the completion of the primary hydrolysis) leads to unsatisfactory results. This 2-step variant (illustrated in Scheme 3 below) results in formation of the desired NR, albeit in low However, zirconium-promoted hydrolysis of NAD⁺ can still be employed in the present invention to achieve reasonable results, (e.g. with $ZrCl_4$, or with $ZrO_2$) if the addition of the phosphate-binding agent source to the reaction vessel is carried out before, or essentially concurrently with, the addition of zirconium. As defined herein "essentially concurrently" means that the phosphate-binding agent source is added simultaneously with the addition of, e.g. $ZrCl_4$, or not more than 0.5-1.0 hours after the addition of $ZrCl_4$. The concentration of $ZrCl_4$ used in this specific variant of the invention is from 15-30 mM. In the so-formed NR-containing aqueous solution the stability of the NR concentrations is about 6 hours, allowing separation and isolation of the product from the zirconium-containing solution.

Without being bound by theory it is believed that the $ZrCl_4$-mediated hydrolysis of NAD⁺ to β-nicotinamide mononucleotide (primary hydrolysis) is significantly faster than the phosphate-binding agent-promoted hydrolysis of the β-nicotinamide mononucleotide to NR (secondary hydrolysis). The lack of synchronization between the reaction rates obviates the accumulation of NR due to tertiary "over-hydrolysis" of NR to the corresponding vitamin PP and ribose (see Scheme 3 above). The experimental results reported herein indicate that it is most preferred to advance the NAD⁺ hydrolysis with the aid of phosphate binding agent alone, that is, in the absence of $ZrCl_4$ or other agent that promotes the primary NAD⁺ hydrolysis.

The concentration of the product (NR) in the resultant aqueous solution may be in the range of 0.5 to 5 mM. For the solution formed on degrading $NAD^+$ with the aid of phosphate-binding agent alone, in the absence of $ZrCl_4$, the concentration of the product remains stable for at least 24 hours (steady-state). As defined herein, the term "stable" refers to a concentration decline of no more than 10% of the product, as measured by one or more of the methods set forth below.

It should be noted that on completion of the reaction, (NR) may be isolated in the form a pharmaceutically or cosmetically acceptable salt thereof using conventional methods. However, a major advantage offered by the present invention is that the resulting β-nicotinamide mononucleotide and/or nicotinamide riboside-containing solution (the NMN- and NR-containing solution) may be formulated directly into a dosage form suitable for oral or topical administration, as a food-additive, pharmaceutical or cosmetic composition, or encapsulated for further formulation, without any separation or further purification of the nicotinamide riboside and/or β-nicotinamide mononucleotide, as described in greater detail below, owing to the fact that the constituents of the mixture derived from the reaction are substances approved by regulatory authorities.

Thus, additional aspects of the invention include a reaction-derived mixture, comprising in an aqueous solvent nicotinamide riboside, $NAD^+$ and/or one or more of the primary, secondary and tertiary hydrolysis-degradation products of $NAD^+$ as described above (that is, β-nicotinamide mononucleotide, adenine mononucleotide, vitamin PP, adenine riboside, ribose) and optionally an excess or traces of the phosphate-binding agent source and/or the precipitate of phosphate salt of the phosphate-binding agent. Additionally, the use of said reaction-derived mixture for the preparation of a dietary supplement, a food additive, a cosmetic or a pharmaceutical composition, preferably in cosmetic composition, is an additional aspect of the invention. The term "reaction-derived" as used herein means that the composition of the product is reaction-determined and not the result of use of downstream steps that can affect the chemical composition of the product. Preferably, the reaction-derived mixture shows acceptable stability of NR.

As mentioned above, the reaction-derived mixture of the invention may be processed according to the intended use, e.g. to produce the solidified reaction-derived mixture. The mixture may be dried by known techniques, e.g. spray-dried or freeze-dried, to furnish the dried reaction-derived mixture. The mixture may also be encapsulated into micron or submicron size capsules, e.g. into silica capsules. The encapsulation may be, e.g. by spray-drying or freeze-drying technique, of said reaction-derived mixture in presence of silica particles of suitable size according of desired particle size of the final product. The reaction-derived mixture may also be encapsulated by a sol-gel methodology, or in microgels, e.g. in Ca(II)/alginate, and in gum arabic particles. Silica particles suitable for the use in these techniques include, but not limited to: colloidal silicon dioxide, fumed silica, e.g. available under trade names Aerosil®, LUDOX®CL, LUDOX®TMA, LUDOX®TM-50, LUDOX®SM, LUDOX®LS, LUDOX®AS-40, and LUDOX®CLX. Additives and surfactants may be used to modify the surface of the microcapsules, e.g. by imparting hydrophobicity.

Freeze-drying may be performed by freezing the reaction-derived mixture, and upon solidification, drying it by ice sublimation. The reaction-derived mixture may also be encapsulated by adding different types of silica particles to the mixture prior to freezing. The freezing may usually be performed at low temperatures (−20 to −195° C.), and the sublimation of the ice under high vacuum, e.g. low pressure. Sometimes, polymeric additives may be included in the mixture before performing the freeze drying process. The suitable additives may include polyethylene glycols (PEG), polyvinyl alcohol (PVA) and derivatives, chitosan, gelatin, cellulose derivatives, gums and alginates.

Spray drying may be performed to obtain the reaction-derived mixture in form of a powder in short time. The aqueous mixture may be passed through a spray nozzle, which creates small droplets with controllable size that are dispersed in a hot stream of air or nitrogen, typically between 20 and 180° C. A rapid drying process of the aqueous droplets occurs (order of 1-10 seconds) and usually particles in the size of the range of 10-500 μm can be obtained. The reaction-derived mixture may also be encapsulated by adding different types of silica particles to the mixture prior to spray-drying. Sometimes, hydrophilic surfactants, e.g. Brij® 78, Tween® 80, or cetyltrimethylammonium bromide, or polymers, e.g. PEG, polyvinyl pyrrolidone (PVP), chitosan, and gelatin, may be added to control the physical and chemical properties of the final particles.

Alternatively, the reaction-derived mixture may be encapsulated by freeze-drying of an emulsified mixture. Silica particles and various additives, e.g. polyethylene glycols, chitosan, gelatin, cellulose derivatives, and gums, may be added to the aqueous solution prior to emulsification and freeze-drying in a suitable oil in the presence of various surfactants proper for the stabilization of w-in-o emulsions, to modify the physical and chemical properties of the resultant particles. The suitable oils include paraffin oil, silicone oil and various vegetable oils. The resulted w-in-o emulsion is frozen and the ice is removed by sublimation, as described above. The resulted particles suspended in oil phase may then be separated by centrifugation, or formulated in a topical preparation.

Silica capsules, e.g. microcapsules or nanocapsules, comprising the reaction-derived mixture may also be prepared by the sol-gel method. The reaction-derived mixture may be dispersed in a suitable oil containing silane monomers. The oil phase is then emulsified in water and an interfacial polycondensation creates a silica shell around the oil droplets. Suitable oils include, for example, silicone oil, paraffin oil and vegetable oils. Suitable silane monomers include tetraethoxysilane (TEOS), tetramethoxysilane, tetrapropoxysilane, methyltriethoxysilane and methyltrimethoxysilane. The emulsification may be assisted with suitable surfactants. After 4-48 hours, a silica shell is formed around the aqueous droplets and silica microcapsules are obtained.

Preferably, the encapsulation of the reaction-derived aqueous solution by sol-gel method may be performed by emulsification of the aqueous solution in oils, e.g. in isopropyl myristate, isononyl isononanoate, paraffin oil, silicone oil, vegetable oils, castor oil as described above and silane monomers, e.g. tetraethoxysilane (TEOS), tetramethoxysilane, tetrapropoxysilane, methyltriethoxysilane and methyltrimethoxysilane, in the presence of hydrophobic surfactants suitable for the stabilization of w-in-o emulsions like Span® 80, Span® 40, Span® 83, Tween 85, Brij® 92, Brij® 96, Montane 70, bis(2-ethylhexyl)sulfosuccinate sodium salt (AOT), Arkopal® N 040, Cremophor® WO7, Cremophor® EL, Arlacel 83, EASYNOV™, ETOCAS 5, ATSURF 5000, HYPERMER B246, LoVOCoat Form 100, ZEPHRYM PD-2206 and ABIL® EM 90. The emulsions may be homogenized using high-shear homogenizers, at speeds of 5,000-20,000 rpm, preferably between 8,000 and 20,000, and may further be sonicated to furnish nanodroplets, using suitable ultrasound equipment, e.g. Sonics Vibralcell VCX 130 Ultrasonic Cell Disruptor. The resultant capsules may be further separated, e.g. by centrifugation, and optionally washed and dried, e.g. by freeze-drying method.

The encapsulation of the reaction-derived mixture by polyurethane encapsulation method may be performed providing glycerol or other polyol monomers (0.1-2 parts) to about 10 parts of aqueous reaction-derived mixture, containing about 2 parts of solutes. The resulted mixture is added to an oil phase containing 10-90 volume parts of isononyl isononanoate or other hydrophobic oils such as isopropyl myristate, paraffin oil, silicone oil, cyclomethicone, olive oil, corn oil, 0.5-1.5 parts of ABIL EM90 or other polymeric surfactants that can stabilize W/O emulsions EASYNOV™, ATSURF 5000, HYPERMER B246, LoVOCoat Form 100, ZEPHRYM PD-2206, and toluene-2,4-diisocyanate (0.2-3 parts) or other isocyanate monomers such as 1,6-hexamethylene diisocyanate, isophorone diisocyanate, diphenylmethane-4,4'-diisocyanate, 1,5-naphthalene-diisocyanate, 3,3'-diisocyanato-4,4'-dimethyl-N,N'-diphenylurea. The resulted mixture is homogenized at 5,000-20,000 rpm and the obtained emulsion is heated at 60-80° C. The resulted polyurethane microcapsules may be isolated from the mixture by centrifugation process.

The encapsulation of the reaction-derived mixture by polyacrylate or poly(methyl methacrylate) encapsulation method may be performed by providing potassium persulfate, ammonium persulfate, 4,4'-azobis(4-cyanovaleric acid) or 2,2'-azobis[2-(2-imidazolin-2-yl)propane]dihydrochloride (0.01-0.5 parts) to about 10 parts of aqueous reaction-derived mixture, containing about 2 parts of solutes. The resulted mixture is added to an oil phase containing 10-90 volume parts of isononyl isononanoate or other hydrophobic oils such as isopropyl myristate, paraffin oil, silicone oil, cyclomethicone, olive oil, corn oil, 0.5-1.5 parts ABIL EM90 or other polymeric surfactants that can stabilize W/O emulsions EASYNOV™, ATSURF 5000, HYPERMER B246, LoVOCoat Form 100, ZEPHRYM PD-2206, and acrylate, methyl methacrylate, acrylamide, hydroxyethyl methacrylate (0.1-5 parts). The resulted mixture is degassed, homogenized at 5,000-20,000 rpm and the obtained emulsion is heated at 60-80° C. under nitrogen. The resulted polyacrylate or poly(methyl methacrylate) microcapsules may be isolated from the mixture by centrifugation process.

The encapsulation of the reaction-derived mixture by hybrid silica/polymer encapsulation method may be performed by providing potassium persulfate, ammonium persulfate, 4,4'-azobis(4-cyanovaleric acid) or 2,2'-azobis-[2-(2-imidazolin-2-yl)-propane]dihydrochloride (0.01-0.5 parts) to about 10 parts of aqueous reaction-derived mixture, containing about 2 parts of solutes. The resulted mixture is added to an oil phase containing 10-90 volume parts of isononyl isononanoate or other hydrophobic oils such as isopropyl myristate, paraffin oil, silicone oil, cyclomethicone, olive oil, corn oil, 0.5-1.5 parts ABIL EM90 or other polymeric surfactants that can stabilize W/O emulsions EASYNOV™, ATSURF 5000, HYPERMER B246, LoVOCoat Form 100, ZEPHRYM PD-2206, and acrylate, methyl methacrylate, acrylamide, hydroxyethyl methacrylate (0.1-5 parts), and tetraethoxysilane (TEOS), tetramethoxysilane, tetrapropoxysilane, methyltriethoxysilane or methyltrimethoxysilane. The resulted mixture is degassed, homogenized at 5,000-20,000 rpm and the obtained emulsion is heated at 60-80° C. under nitrogen. The resulted hybrid silica/polymer microcapsules may be isolated from the mixture by centrifugation process.

The encapsulation of the reaction-derived mixture by Pickering encapsulation may be performed by providing about parts of aqueous reaction-derived mixture, containing about 2 parts of solutes, to an oil phase containing 10-90 volume parts of isononyl isononanoate or other hydrophobic oils such as isopropyl myristate, paraffin oil, silicone oil, cyclomethicone, olive oil, corn oil, 0.1-5 parts of hydrophobic silica particles, Latex particles, $TiO_2$ particles or $Al_2O_3$ particles. The resulted mixture is homogenized at 5,000-20,000 rpm to yield the Pickering capsules. The resulting capsules may be separated, e.g. by filtration.

The reaction-derived mixture may also be encapsulated in microgels, e.g. calcium alginate, or in gum arabic (gum acacia) particles. The w/o emulsion may be formed by dissolving the alginate/alginic acid or the gum in water, and suspending the aqueous solution in a suitable oil comprising at least one hydrophobic surfactant with low HLB value e.g. 1 to 10, preferably 3 to 7, that may include, e.g. Span® 80 and Brij® 92. The reaction-derived mixture is then added to the w/o emulsions. The reaction-derived mixture may contain an excess of the phosphate-binding agent source, e.g. a calcium salt. Alternatively or additionally, additional amounts of calcium salts may be added to the w/o emulsion. Resultant particles may be separated, e.g. by centrifugation.

For the preparation of topical preparations, e.g. creams, serums, lotions or gels, the reaction-derived mixture may be used in an encapsulated form. For example, the reaction-derived mixture is provided in a sol-gel silica capsules, either neat or in an oil. In particularly preferred embodiments, the reaction-derived mixture is incorporated in a cosmetic semisolid or liquid product, e.g. creams, serums, lotions, gels, etc.

Generally, the reaction-derived mixture either in free or encapsulated form, may be incorporated into topical cosmetic preparations, which are prepared as generally known in the art, e.g. following the guidance of *Remington: The Science and Practice of Pharmacy*, $21^{st}$ edition, ISBN 0-7817-4673-6, and/or *Handbook of Cosmetic Science and Technology*, $3^{rd}$ edition, ISBN 1-4200-6963-2, and along the lines of exemplified cosmetic products, e.g. in *Cosmetic and Toiletry Formulations*, $2^{nd}$ edition, ISBN 0-8155-1306-2. More specifically, the water-soluble components are dissolved together in water, and oil-soluble components are dissolved/co-melted separately from the water-soluble components, and then combined at suitable temperature and agitation/homogenization. The reaction-derived mixture or encapsulated mixture may be incorporated into the resulting composition, and mixed to homogeneity.

Transdermal dosage forms may be prepared by incorporating the reaction-derived mixture in an oily semi-solid preparation, e.g. oily cream or an ointment, comprising suitable permeation enhancers and/or emollients, or in a suitable patch as known in the art.

For the preparation of oral dosage forms, e.g. capsules or tablets, the reaction-derived mixture may be used in any of the described forms, e.g. spray-dried, freeze-dried form, or an encapsulated form. The dry powder may be processed as known in the art. Alternatively, the mixture may be used as granulation liquid on a suitable carrier, e.g. lactose, microcrystalline cellulose, or calcium phosphate.

As mentioned above, the reaction-derived mixture of the invention is used in commercial applications, either as such or in an encapsulated form. Without being bound by theory, it is believed that the reaction-derived mixture of the invention is useful for re-synthesis back into $NAD^+$ within the body, by the cells, especially because it comprises a mixture/combination of several β-nicotinamide adenine dinucleotide (NAD⁺) precursors. Examples of commercial applications include, without being limited to, preparation of a dietary supplement, preparation of a food additive, and preferably preparation of a cosmetic or of a medicament for treatment of a disease or condition. Non-limiting example of diseases or conditions are aging, energizing, detoxification and DNA repair, obesity, cognition, sleep and metabolism-related problems.

Thus, according to another aspect, provided herein is a cosmetic composition comprising nicotinamide riboside (NR) and/or β-nicotinamide mononucleotide, produced according to the process of the invention, wherein the process comprises reacting a nicotinamide riboside precursor, e.g. β-nicotinamide adenine dinucleotide (NAD⁺), and a source of phosphate-binding agent. Preferably, the cosmetic product may contain or be labeled to contain nicotinamide riboside, and/or at least one of NAD⁺ and β-nicotinamide mononucleotide, or at least one degradation product thereof, and optionally further a phosphate-binding agent, e.g. in form of a water-soluble salt, e.g. calcium salt, as described above, and/or water-insoluble phosphate salt of said phosphate-binding agent, e.g. calcium phosphate. Preferably, the cosmetic product may be zirconium free.

According to another aspect, provided herein is a nutraceutical composition comprising nicotinamide riboside (NR) and/or β-nicotinamide mononucleotide, produced according to the process of the invention, wherein the process comprises reacting a nicotinamide riboside precursor, e.g. β-nicotinamide adenine dinucleotide (NAD⁺), and a source of phosphate-binding agent.

According to yet another aspect, provided herein is a pharmaceutical composition comprising nicotinamide riboside (NR) and/or β-nicotinamide mononucleotide, produced according to the process of the invention, wherein the process comprises reacting a nicotinamide riboside precursor, e.g. β-nicotinamide adenine dinucleotide (NAD⁻) and a source of phosphate-binding agent.

According to additional aspect, provided herein is a dietary supplement comprising nicotinamide riboside (NR) and/or β-nicotinamide mononucleotide, produced according to the process of the invention, wherein the process comprises reacting a nicotinamide riboside precursor, e.g. β-nicotinamide adenine dinucleotide (NAD⁺) and a source of phosphate-binding agent.

According to additional aspect, provided herein is a food additive comprising nicotinamide riboside (NR) and/or β-nicotinamide mononucleotide, produced according to the process of the invention, wherein the process comprises reacting a nicotinamide riboside precursor, e.g. β-nicotinamide adenine dinucleotide (NAD⁺) and a source of phosphate-binding agent.

According to additional aspect, provided herein is a medicament comprising nicotinamide riboside (NR) and/or β-nicotinamide mononucleotide, produced according to the process of the invention, wherein the process comprises reacting a nicotinamide riboside precursor, e.g. β-nicotinamide adenine dinucleotide (NAD⁺) and a source of phosphate-binding agent.

As described above, the nicotinamide riboside (NR) and/or β-nicotinamide mononucleotide produced according to the process of the invention or the reaction-derived mixture of the invention is formulated for a topical use as skin-care or skin medication, for example in the form of a cream, serum, lotion or gel. Such formulations may be useful for fast administration of β-nicotinamide adenine dinucleotide (NAD⁺) precursors to the dermis, and also transdermally to the circulation.

EXAMPLES

Materials

The nicotinamide adenine dinucleotide (NAD⁺), β-nicotinamide mononucleotide, adenine monophosphate and nicotinamide (vitamin PP) standards were purchased from the Sigma Aldrich. Nicotinamide riboside (NR) was purchased from ChromaDex.

Methods

Mass Spectrometry (MS), High Performance Liquid Chromatography (HPLC) and Nuclear Magnetic Resonance Spectroscopy (NMR) based detection methods were developed for each one of the materials.

NMR spectra were recorded with 400 MHz Bruker spectrometer. Reversed phase HPLC column of RP-18 type (Chromolith performance RP18e (100-4.6 mm) UM8 086/001, Merck KGaA) using deionized HPLC-grade solvents in the following composition: 1% acetonitrile, 99% water. Flow rate was 0.1 mL/min, detection performed with UV detector at 260 nm. Mass Spectrometry (MS), 6200 series TOF/6500 series Q-TOF B.05.01 (B5125.1).

HPLC-based method alone was found insufficiently accurate for unequivocal identification of the desired nicotinamide riboside (NR) due to similar retention times of the nicotinamide mononucleotide and NR under all tested separation conditions. The best separation was achieved using reversed phase HPLC column of RP-18 type (Chromolith performance RP18e (100-4.6 mm) UM8 086/001, Merck KGaA) using deionized HPLC-grade solvents in the following composition: 1% acetonitrile, 99% water. Flow rate was 0.1 mL/min, detection performed with UV detector at 260 nm. HPLC retention times under these conditions are provided in Table 1.

TABLE 1

| Material | HPLC retention time (minutes) |
| --- | --- |
| NAD⁺ | 24.91 |
| Adenosine | 20.77 |
| β-nicotinamide mononucleotide | 14.52 |
| nicotinamide riboside | 15.18 |
| Vitamin PP | 37.27 |

Despite nicotinamide mononucleotide and NR significant overlap, it is possible to distinguish between the two by spiking experiment (e.g. intentionally spiking the commercial NR standard into actual sample to confirm that the intensity of the observed overlapped peaks changes accordingly). The resulting HPLC chromatograms demonstrate that β-nicotinamide mononucleotide+nicotinamide riboside (NR) were separated with retention times 14.52 min and 15.18. After spiking with NR (higher intensity) the chromatogram shows major peak at 15.18 minutes. After spiking with β-nicotinamide mononucleotide (separation) two major peaks are observed at 14.52 minutes and 15.18 minutes.

Proton NMR ($^1$H NMR) and $^{31}$-phosphorus NMR ($^{31}$P-NMR) allow distinguishing between the starting material NAD⁺, the intermediate nicotinamide mononucleotide and the desired product nicotinamide riboside (NR). NAD⁺ and nicotinamide mononucleotide are characterized by very distinguishable $^{31}$P-NMR signals ($^{31}$P NMR shifts are −11.36 and −11.65, and −0.08 ppm, respectively), while the desired NR is $^{31}$P-NMR-silent (see Scheme 4).

(Scheme 4)

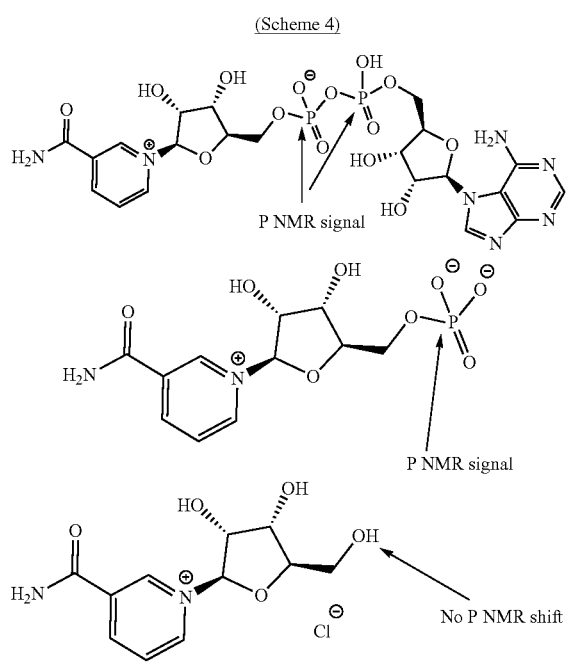

Further decomposition of NR to ribose and nicotinamide (vitamin PP) is possible as NR is unstable over prolonged exposure to acidic or basic (hydrolytic) conditions. Proton NMR ($^1$H NMR) is indicative in tracing the decomposition process of NR (see Scheme 5).

(Scheme 5)

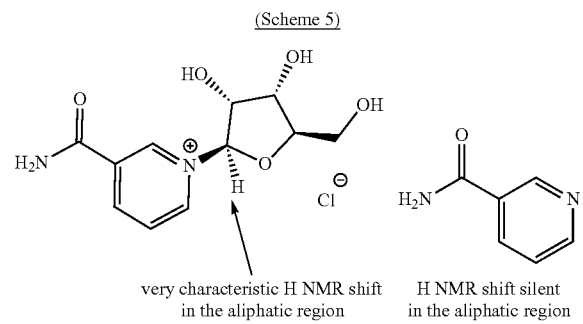 [SMILES: NC(=O)c1ccc[n+]([C@@H]2O[C@H](CO)[C@@H](O)[C@H]2O)c1 ; [Cl-] ; NC(=O)c1cccnc1]

$^1$H-NMR spectrum of nicotinamide riboside reveals the following peaks: 3.88 (2H, dd, $J_{1,2}$=62.25 Hz, $J_{1,3}$=3.55 Hz), 4.26 (1H, t, J=4.63 Hz), 4.37-4.39 (1H,m), 4.41 (1H, t,J=4.47 Hz), 6.15 (1H, d, J=4.47 Hz), 8.17 (1H, t, J=6.81 Hz), 8.88 (1H, d, J=8.17 Hz), 9.18 (1H, d, J=8.18 Hz), 9.51 (1H, s).

$^1$H-NMR spectrum of Vitamin PP reveals the following peaks: 7.44 (1H,dd, J=8.59, 5.9 Hz), 8.09 (1H,dt, J=8.09, 1.95 Hz), 8.56 (1H,dd, J=5.10, 1.6 Hz), 8.78 (1H,d, J=2.15 Hz).

However, the ultimate identification of the desired product (NR) was performed using High Resolution-Mass Spectrometry (HR-MS) technique. Calculated molecular weight (MW) for the formula $C_{11}H_{15}N_2O_5^+$ is 255.0975. Found MW is 255.09285.

Example 1 (Comparative)

Preparation of Nicotinamide Riboside from NAD$^+$ by a Two-Stage Process (ZrCl$_4$-Promoted NAD$^+$ Primary Hydrolysis Followed by Secondary Hydrolysis Stage one: In a 250-ml flask, to a mixture of NAD$^+$ (0.3317 gr) and ZrCl$_4$ (0.582 gr), 100 ml of deionized water was added and the reaction was heated to 80° C. for 30 minutes. Over this time, full conversion of the NAD to β-nicotinamide mononucleotide was observed by HPLC.

Stage two: 1.8 gr of calcium L-ascorbate dihydrate was added to the reaction mixture and heating was continued for further 2 days at 80° C.

Samples from the reaction mixture were analyzed every 4-5 hours by HPLC and NMR. Formation of the desired NR was detected albeit in low concentration (lower than 3% yield) due to extensive decomposition of NR to ribose and nicotinamide. HR-MS spectrum of the product of Stage 2 is with MW of 255.16. The yield was determined by comparing the abundance of the desired peak to the abundance of the internal standard.

Example 2

Preparation of Nicotinamide Riboside from NAD$^+$ by a One-Stage Process (ZrCl$_4$-Promoted Primary NAD$^+$ Hydrolysis and Secondary Hydrolysis Carried Out Concurrently In order to reduce the extent of the NR decomposition via tertiary "over-hydrolysis", one stage protocol was developed.

In a 250-ml flask, a mixture of NAD$^+$ (0.33 gr), ZrCl$_4$ (0.58 gr) and 1.80 gr of calcium L-ascorbate in 100 ml of deionized water was heated to 80° C. for 2 days. Over this time period, full conversion of the NAD$^+$ was observed by HPLC. Decomposition of the desired NR product was also observed under these conditions, but to a lower extent in comparison with the process of Example 1. HR-MS spectrum of the product is MW of 255.10. The extent of the decomposition of the desired NR was determined by comparing the abundance of the desired peak to the abundance of the internal standard.

The concentrations of the products and the reactants at various time points are provided in Table 2.

TABLE 2

| Time (hours) | NAD$^+$ Relative Concentration | NR Relative Concentration | Nicotinamide |
| --- | --- | --- | --- |
| 0 | 1 | 0 | 0 |
| 0.5 | 0.66 | 0.05 | 0.1 |
| 6 | 0.32 | 0.06 | 0.19 |
| 16 | 0.05 | 0.02 | 0.32 |
| 24 | 0 | 0 | 0.48 |

Example 3

Preparation of Nicotinamide Riboside from NAD$^+$ with the Aid of Phosphate Binding Agent Alone In a 250-ml flask, a mixture of NAD$^+$ (0.34 gr) and 1.8 gr of calcium L-ascorbate in 100 ml of deionized water was heated to 80° C. for 4 days. The mixture was analyzed every 3 hours using HPLC and $^{31}$P-NMR. According to HPLC analysis and $^{31}$P NMR, in the absence of ZrCl$_4$, the rate of the primary hydrolysis of NAD$^+$ to β-nicotinamide mononucleotide was slow and comparable to the rate of the secondary hydrolysis of the β-nicotinamide mononucleotide to the NR. The concentrations of the products and the reactants at various time points are provided in Table 3.

TABLE 3

| Time (hours) | NAD$^+$ Relative Concentration | NR Relative Concentration | Nicotinamide |
| --- | --- | --- | --- |
| 0 | 1 | 0 | 0 |
| 0.5 | 0.86 | 0.06 | 0.1 |

TABLE 3-continued

| Time (hours) | NAD$^+$ Relative Concentration | NR Relative Concentration | Nicotinamide |
|---|---|---|---|
| 6 | 0.62 | 0.11 | 0.16 |
| 16 | 0.55 | 0.09 | 0.32 |
| 24 | 0.38 | 0.08 | 0.48 |
| 36 | 0.22 | 0.01 | 0.41 |
| 48 | 0.2 | 0 | 0.41 |

HR-MS spectrum of the product, as taken at the end of the reaction yielded MW of 255.09495. Calculated MW for the formula $C_{11}H_{15}N_2O_5^+$ is 255.0975.

The rate of the tertiary hydrolysis (decomposition of the NR) is slower. Under these conditions, the concentration of the NR remains essentially stable (~10% decline) over 24 hours (steady-state). The concentration was determined by comparing the abundance of the desired peak to the abundance of the internal standard MS and $^1$H- and $^{31}$P-NMR (intensity of the signal). After this time the concentration of the NR decreased and the product was no longer present. The concentrations of the products and the reactants at various time points are provided in Table 3.

Additionally, to establish the stability of the commercial NR product (Niagen® purchased from ChromaDex) under hydrolytic conditions, it was dissolved in deionized water as described herein and the mixture was analyzed every 3 hours using $^1$H- and $^{31}$P-NMR. The $^1$H-NMR spectra obtained after 0.5 hours, 6 hours and 24 hours demonstrate two peaks ma at 6.15 ppm (1H,d, J=5.38 Hz) that represents the NR compound and 7.78 (1H,s) represents the DMF solvent (dimethylformamide) which was used as an internal standard in (1:1) ratio to help us following the decay of the NR peak at 0.5 hours, at 6 hours the NMR shifts and splits were the same but the intensity of the NR peak decreased compared to the DMF, and after 24 hours the peak in 6.15 ppm was not observed, signifying that NR has degraded. The data for various time points are provided in Table 4.

TABLE 4

| Time (hours) | NR (Niagen ®) relative concentration |
|---|---|
| 0.5 | 1 |
| 3 | 0.62 |
| 6 | 0.48 |
| 24 | 0.02 |
| 48 | 0 |

Example 4

Preparation of Silica Capsules Containing Reaction-Derived Mixture of NAD$^+$ and Phosphate Binding Agent Step 1 (Reaction-Derived Mixture):
A 10-mL vial was loaded with 0.33 g of NAD$^+$, 1.8 g of calcium L-ascorbate dihydrate. The powders were dissolved with 8.2 mL of distilled water and the mixture was heated at 80° C. for 24 hours.

Step 2 (Capsules Formation):
The resultant mixture from the step 1 was cooled to room temperature, and subsequently added to a 250-mL flask, containing a solution of 77.65 g of isononyl isononanoate (SABODERM ISN oil, manufactured by SABO S.p.A), 0.5 g ABIL EM90 (cetyl PEG/PPG-10/1 Dimethicone, manufactured by Evonik Industries AG Personal Care) and 11.85 g of tetraethoxysilane (TEOS). The mixture was homogenized by homogenizer at 10,000 rpm for 5 minutes, with Polytron PT-6100 homogenizer, manufactured by Kinematica, equipped with 20-mm PT-DA standard-type head/shaft (PT-DA 3020/2EC; product number 9115128).

The obtained w/o emulsion was stirred at room temperature using magnetic stirrer for 24 hours to yield silica microcapsules. The microcapsules were then separated from the reaction mixture by centrifugation using 29×32×25-cm HSCEN-204 centrifuge, at 5000 rpm, washed 3 times with diethyl ether, and finally dried in a Memmert Beschickung loading model 100-800 oven (Memmert GmbH) at 54±0.1° C. for 24 h.

SEM evaluation of the particles was conducted using high resolution scanning electron microscope (HR SEM) Sirion (FEI Company) using Shottky type field emission source and secondary electron (SE) detector. The images were scanned at voltage of 5 kV. TEM evaluation was performed at (S) Tecnai F20 G$^2$ instrument (FEI company) operated at 200 kV.

SE micrographs reveal capsules of size between 0.8-5.0 μm, of essentially spherical in shape, with mildly negative zeta potential of −25.4±13.0 mV. TE micrographs demonstrate capsules with a shell around, with some degree of roughness.

Example 5

Preparation of Silica Capsules Containing Reaction-Derived Mixture of NAD$^+$ and Phosphate Binding Agent, with Smaller Particle Size Step 1:
The materials were used as in Example 4, and the preparation was repeated according to step 1 thereof.

Step 2 (Nanocapsules Formation):
The resultant mixture from the step 1 was cooled to room temperature, and subsequently added to a 250-mL flask, containing a solution of 77.65 g of isononyl isononanoate (SABODERM ISN oil, manufactured by SABO S.p.A), 0.5 g ABIL EM90 (cetyl PEG/PPG-10/1 Dimethicone, manufactured by Evonik Industries AG Personal Care) and 11.85 g of tetraethoxysilane (TEOS). The mixture was homogenized by homogenizer at 10,000 rpm for 5 minutes, with Polytron PT-6100 homogenizer, manufactured by Kinematica, equipped with 20-mm PT-DA standard-type head/shaft (PT-DA 3020/2EC; product number 9115128), and further sonicated for 30 minutes using Sonics Vibralcell VCX 130 Ultrasonic Cell Disruptor with an output of 130 W and 20 kHz.

The obtained w/o emulsion was stirred at room temperature using magnetic stirrer for 24 h to yield silica capsules. The capsules were then separated from the reaction mixture by centrifugation using 29×32×25-cm HSCEN-204 centrifuge, at 5000 rpm, washed 3 times with diethyl ether, and finally dried in a Memmert Beschickung loading model 100-800 oven (Memmert GmbH) at 54±0.1° C. for 24 h.

SEM evaluation of the particles was conducted using high resolution scanning electron microscope (HR SEM) Sirion (FEI Company) using Shottky type field emission source and secondary electron (SE) detector. The images were scanned at voltage of 5 kV. Particles' morphology, SEM, TEM and zeta potential were similar to the particles of the Example 4, with particle size 200-500 nm.

Example 6

Preparation of β-Nicotinamide Mononucleotide

A 10-mL vial was loaded with 0.33 g of NAD$^+$, 0.29 g of zirconium dioxide (ZrO$_2$). The powders were dissolved/dispersed with 9.5 mL of distilled water, and the mixture was heated at 80° C. for 48 h. ZrO$_2$ was removed by centrifugation (10,000 rpm for 30 min) using 29×32×25-cm HSCEN-204 centrifuge.

The $^{31}$P-NMR demonstrated a small peak at −11.15 ppm, attributed to NAD$^+$, a peak at −0.03 ppm attributed to β-nicotinamide mononucleotide, a peak at 0.09 ppm attributed to adenosine, and two peaks at 0.027 and 0.3 ppm, attributed to the two P atoms of adenosine diphosphate (ADP).

Example 7

Direct Incorporation of an Encapsulated NR Mixture into a Cosmetic Preparation (Cream)

Reaction-derived mixture was obtained as silica capsules dispersion according to the Steps 1 and 2 of the Example 4 above. The capsules were separated and were applied as described below.

Separately, water, propanediol, potassium cetyl phosphate, allantoin, and glycerin were combined together at 75° C. in the main vessel of 10-L reactor, in relative amounts of 62.6:3.0:0.5:0.2:4.0, respectively. In the side vessel, the components cetearyl alcohol/cetearyl glucoside mixture (provided as Montanov 68 product), isononyl isononanoate, cyclomethicone, cetearyl ethylhexanoate, cetyl alcohol, triethanolamine, and butyrospermum parkii (shea butter) were mixed at 75° C., in relative amounts of 5.0:5.0:6.0:4.0:2.5: 0.1:1.0, respectively. The components of the side reactor were introduced into the main reactor under homogenization, and further mixed for 20 minutes. The temperature was then cooled to below 50° C., and a mixture of phenoxyethanol/ethylhexylglycerin (provided as Euxil PE-9010 product), and fragrance (provided as Fragrance Rich Beauty product), in relative amounts of 1.0:0.1 parts were added, and mixed and homogenized for further 10 minutes. Finally, the temperature was lowered to below 40° C., and the encapsulated reaction-derived mixture in oil was, consisting of silica/calcium-l-ascorbate/NAD$^+$/isononyl isononanoate/ mixture of cetyl PEG/PPG-10/1 dimethicone, as described in greater detail in the example 4 above. The mixture in the vessel was slowly mixed for additional 5 minutes, and the resultant product was transferred for packaging.

The invention claimed is:

1. A process for preparing nicotinamide riboside (NR), wherein said process is a chemical synthesis process performed at a temperature between 40 to 90° C. inclusive, the process comprising combining an NR precursor which is β-nicotinamide adenine dinucleotide (NAD$^+$), with a phosphate-binding agent in a solvent, wherein said solvent comprises water, and wherein said phosphate binding agent is a salt of Ca($^{2+}$).

2. The process according to claim 1, wherein in said solvent said salt of Ca($^{2+}$) forms a salt having solubility-product constant ($K_{sp}$) of lower than $10^{-16}$ with phosphate anion.

3. The process according to claim 1, wherein salt of Ca($^{2+}$) is a water-soluble salt having a water solubility at room temperature of above 3 g per 100 g of water.

4. The process according to claim 3, wherein molar ratio between said NR precursor and said salt of Ca($^{2+}$) is between 1:2 and 1:15, inclusive.

5. The process according to claim 1, further comprising combining a zirconium salt essentially concurrently with said phosphate binding agent.

6. The process according to claim 5, wherein the process as a whole is performed for no more than 6 hours.

* * * * *